US007721730B2

(12) United States Patent
Hamano et al.

(10) Patent No.: US 7,721,730 B2
(45) Date of Patent: May 25, 2010

(54) LIQUID EJECTION APPARATUS

(75) Inventors: Soji Hamano, Yokohama (JP); Mitsuru Imai, Chichibu (JP)

(73) Assignee: Canon Kabushiki Kaisha, Tokyo (JP)

(*) Notice: Subject to any disclaimer, the term of this patent is extended or adjusted under 35 U.S.C. 154(b) by 857 days.

(21) Appl. No.: 11/535,460

(22) Filed: Sep. 26, 2006

(65) Prior Publication Data

US 2007/0076067 A1 Apr. 5, 2007

(30) Foreign Application Priority Data

Oct. 4, 2005 (JP) ............................ 2005-290603

(51) Int. Cl.
*A61M 11/00* (2006.01)

(52) U.S. Cl. ............................ 128/200.14; 128/200.24; 128/200.23; 128/200.16; 128/200.19; 128/200.21

(58) Field of Classification Search ............ 128/200.14, 128/200.16, 200.19, 200.21, 200.23, 200.24
See application file for complete search history.

(56) References Cited

U.S. PATENT DOCUMENTS

| | | | | |
|---|---|---|---|---|
| 5,604,928 | A | 2/1997 | Hamano et al. | |
| 6,435,175 | B1 * | 8/2002 | Stenzler | 128/200.14 |
| 6,637,430 | B1 | 10/2003 | Voges et al. | 128/200.14 |
| 2002/0041296 | A1 | 4/2002 | Nagatomo et al. | 347/9 |
| 2002/0195101 | A1 * | 12/2002 | Scheuch | 128/200.14 |
| 2003/0140921 | A1 * | 7/2003 | Smith et al. | 128/200.14 |
| 2003/0183226 | A1 * | 10/2003 | Brand et al. | 128/200.23 |
| 2005/0067503 | A1 | 3/2005 | Katase | 239/373 |

FOREIGN PATENT DOCUMENTS

| | | |
|---|---|---|
| JP | 2002/165882 | 6/2002 |
| WO | 95/01137 | 1/1995 |
| WO | 02/04043 | 1/2002 |
| WO | 03/005950 | 1/2003 |

* cited by examiner

*Primary Examiner*—Justine R Yu
*Assistant Examiner*—Colin Stuart
(74) *Attorney, Agent, or Firm*—Fitzpatrick, Cella, Harper & Scinto

(57) ABSTRACT

An ejection apparatus for ejecting droplets of liquid includes a loading portion, a reader, and a judging unit. The loading portion detachably loads therein a liquid cartridge container for containing liquid, and a liquid ejection cartridge having an ejecting portion for ejecting liquid separately, or as a combined kit. The reader reads information attached to at least one of the liquid cartridge container and the liquid ejection cartridge. The judging unit judges, based on the information read by the reader, whether each of the liquid cartridge container and the liquid ejection cartridge loaded in the loading portion is appropriate, or whether a combination of the liquid cartridge container and the liquid ejection cartridge is a predetermined combination. The ejection apparatus allows a user to relatively readily and accurately carry out ejection of appropriate liquid by an appropriate ejection unit.

13 Claims, 11 Drawing Sheets

LIQUID EJECTION APPARATUS

BACKGROUND OF THE INVENTION

1. Field of the Invention

The present invention relates to a liquid ejection apparatus, such as an inhaler capable of enabling a user to inhale liquid, typically liquid containing physiologically active substance, such as medicament or drug, as droplets.

2. Description of the Related Background Art

In recent years, as medical and other sciences advance, average life expectancy increases and an aging society is coming nearer. At the same time, people's dietary habits and living environment are changing, and environmental pollution becomes more serious. Further, new illnesses and infectious diseases due to viruses and bacteria are discovered, and people's uneasiness for health grows stronger. Particularly, in developed countries, the number of individuals suffering from lifestyle-related illnesses, such as diabetes and high blood pressure, increases considerably.

On the other hand, the number of medical institutions is not increasing so fast as can deal with increase in the number of people suffering from the above illnesses. There exist even such areas as cannot provide medical institutions at which each individual can see a doctor regularly. Therefore, appropriate future measures including policy are desired strongly.

Exemplified cases will be described. Among patients of diabetes the number of which is presently increasing, patients of I-type diabetes, i.e., insulin dependent diabetes, have pancreas incapable of secreting insulin. Hence, those patients should receive regular administration of insulin. Presently, dosing of insulin is executed by hypodermic injection. Physical and mental burdens of users are accordingly seriously heavy.

To lighten those burdens of users, there has been developed a pen-type syringe with a thin needle and with little attendant pain. Patients of I-type diabetes mostly live ordinary lives similar to those of healthy people, with the exception that the patients should receive regular administration of insulin. Therefore, even in the case of the pen-type syringe, patients naturally undergo mental hardship of injection before the presence of other people. It is thus difficult for those patients to do self-administration of insulin at appropriate times. Consequently, there is a possibility of inappropriate treatment of patients using such a method.

Further, treatment of users capable of making use of information database, such as an electronic patient's case record, is being coming true by means of a medicament inhaler for dosing a user with medicament through inhalation. Such a medicament inhaler is equipped with a memory unit for storing information about an individual, such as data of user's case record and data of user's prescription, and an ejecting unit for ejecting liquid medicament as minute droplets. The medicament inhaler further includes an ejection control unit for controlling the ejecting unit according to a user's inhalation profile to eject the medicament so that the user can inhale the medicament in accordance with the information of the prescription. In this connection, see PCT International Publication Nos. WO 95/01137, and WO 02/04043.

With such a medicament inhaler, the number of kinds of medicaments or medicines capable of being dosed is increasing. In such a situation, countermeasures for preventing an erroneous loading or installation of a medicament container or tank are required. For those purposes, there has been proposed such an inhaler that includes a tank with a code for distinguishing or discriminating the kind of medicament stored therein, an ejecting head for ejecting liquid medicament supplied from the tank as droplets, and an ejection permitting unit. The ejecting permitting unit reads the above code, and puts the ejecting unit in an operable condition only when the medicament stored in the tank is compared with, and found to coincide with medicament described in information of a prescription stored in the memory unit. In this connection, see Japanese Patent Application Laid-open No. 2002-165882.

Patients or users of medicament inhalers are often elderly people who suffer from plural diseases and troubles. Those users frequently must inhale a plurality of kinds of medicaments. In such a case, appropriate administration parts of a body of the user can vary according to the kind of medicament. A most important factor for determining the medicament dosage part of a body is the size of a liquid medicament droplet being ejected from the medicament inhaler. For example, the diameter of the droplet is said to be preferably about three (3) microns for absorption via pulmonary route, and if the diameter is larger than that, droplets are liable to be stopped at bronchia and so forth. Conversely, in order to cause the droplets to act at bronchia, the diameter of the droplet is preferably about five (5) microns. If the diameter of the droplet is less than one (1) micron, its value is too small. The droplets are surely exhausted from the body along with user's exhalation. In other words, there are cases where medicament is subjected to topical application as in bronchial diseases, and where medicament is administered to the entire body through pulmonary alveoli and blood flow as in diabetes using insulin, and a suitable diameter of liquid medicament droplet varies according to cases.

Further, there is a variation between individuals. For example, a location of the body where drug reaches varies between individuals even when the diameter of liquid medicament droplet is the same. Appropriate diameters of medicament droplets for achieving their medical effects can thus vary among individual users.

Generally, it is necessary to change the diameter of a nozzle disposed at an ejecting end portion of a medicament ejection cartridge in order to adjust the above-discussed diameter of the liquid medicament droplet. Such necessity, however, causes occurrence of innumerable combinations of liquid medicament cartridge tanks and medicament ejection cartridges. This situation imposes annoying or troublesome management and carefulness on users, and brings forth a possibility of impediment of appropriate inhalation. These matters are critical for users.

It is hence preferable to provide a liquid medicament container or tank and a medicament ejection head separately, considering the fact that there are cases where various kinds of medicaments need to be ejected as droplets with appropriate diameters, where an individual patient should inhale plural kinds of liquid medicaments, and where a plurality of users employ a common inhaler. Such separate preparation increases the number of combinations, and allows appropriate combinations to be used in accordance with various cases.

In the above situation, however, plural liquid medicament cartridge tanks and plural ejection cartridges must be prepared, leading to not only annoying or troublesome management, but also impediment of appropriate inhalation caused by selection of an erroneous combination, as discussed above. With the inhaler of the above-mentioned Japanese Patent Application Laid-open No. 2002-165882 using a tank with a code for distinguishing plural kinds of medicaments from one another, it is possible to prevent an erroneous loading of the liquid medicament tank, but difficult to cope with the above-discussed problems.

SUMMARY OF THE INVENTION

It is an object of the present invention to provide liquid ejection apparatuses, such as inhalers, capable of coping with the above-discussed problems, and allowing users to relatively readily and accurately carry out ejection of appropriate liquid by an appropriate ejection unit in accordance with a case. It is another object of the present invention to provide liquid ejection cartridges capable of coping with the above-discussed problems.

According to one aspect of the present invention, there is provided an ejection apparatus for ejecting droplets of liquid, which includes a loading portion, a reader, and a judging unit. The loading portion detachably loads therein a liquid cartridge container for containing a liquid, and a liquid ejection cartridge having an ejecting portion for ejecting the liquid. The reader reads information attached to each of the liquid cartridge container and the liquid ejection cartridge. The judging unit judges, based on the information read by the reader, at least one of (i) whether the liquid cartridge container is a predetermined liquid cartridge container and the liquid ejection cartridge is a predetermined liquid ejection cartridge, and (ii) whether a combination of the liquid cartridge container and the liquid ejection cartridge is a predetermined combination. An exemplified construction of the ejection apparatus of this type is described in a later-described first embodiment.

According to another aspect of the present invention, there is provided an ejection apparatus ejecting droplets of liquid, which includes a loading portion, a reader, and a judging unit. The loading portion detachably loads therein a liquid cartridge container for containing liquid, and a liquid ejection cartridge having an ejecting portion for ejecting liquid. Each of the liquid cartridge container and the liquid ejection cartridge has a coupler that allows interconnection between the liquid cartridge container and the liquid ejection cartridge only when a combination of the liquid cartridge container and the liquid ejection cartridge is a predetermined combination. The reader reads information attached to one of the liquid cartridge container and the liquid ejection cartridge. The judging unit judges, based on the information read by the reader, whether the liquid cartridge container is a predetermined liquid cartridge container and the liquid ejection cartridge is a predetermined liquid ejection cartridge. An exemplified construction of the ejection apparatus of this type is described in a later-described second embodiment.

According to still another aspect of the present invention, there is provided a liquid ejection cartridge that includes an ejecting portion constructed to eject liquid, and a portion with information of at least one of the liquid ejection cartridge and a liquid cartridge container that is to be interconnected with the liquid ejection cartridge.

Other features and advantages of the present invention will be apparent from the following description taken in conjunction with the accompanying drawings, in which like reference characters designate the same or similar parts throughout the figures thereof.

DESCRIPTION OF THE EMBODIMENTS

Figure 1:
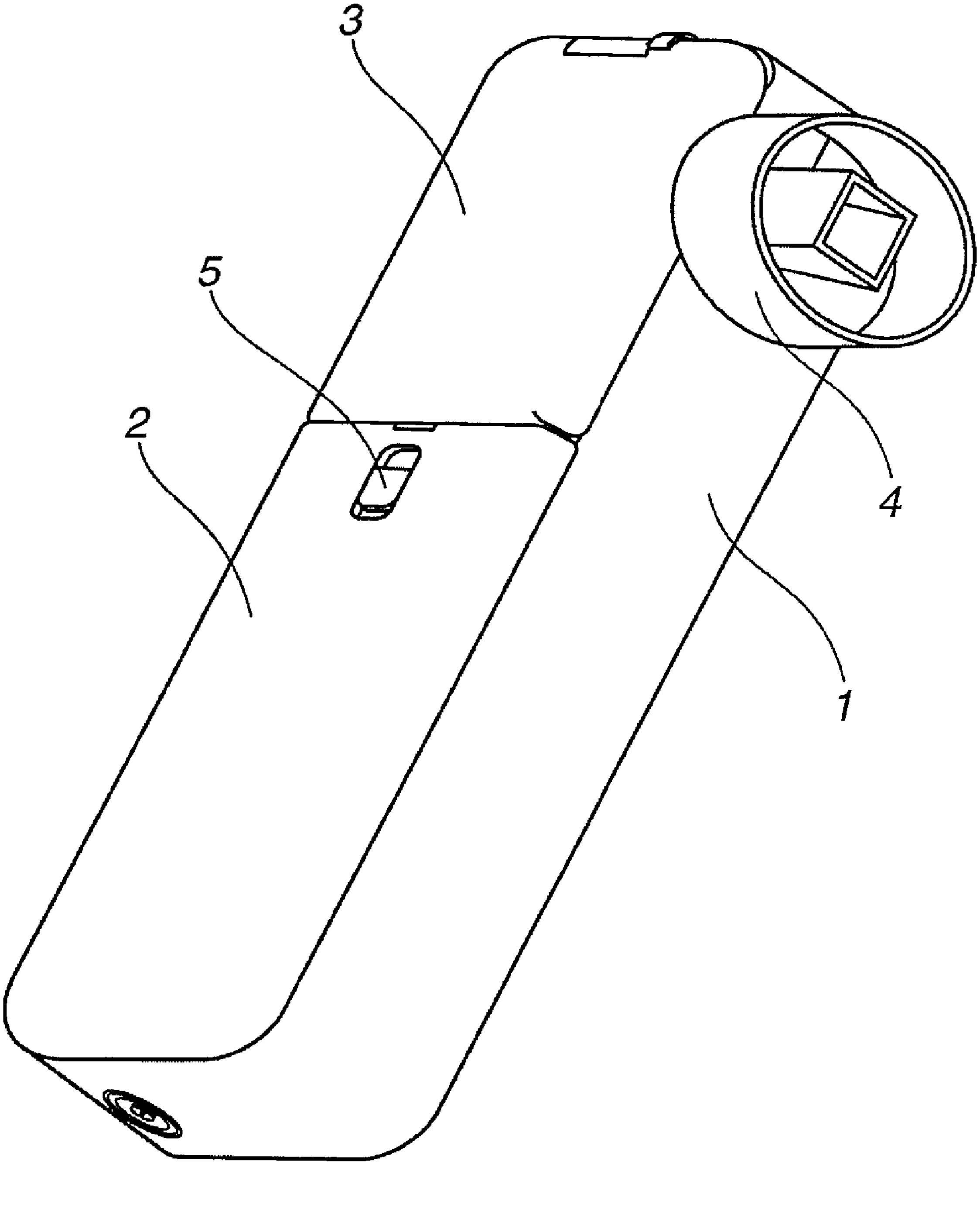
FIG. 1 is a perspective view schematically illustrating the outside appearance of an embodiment of an inhaler according to the present invention.

Preferred embodiments of the present invention will now be described in detail in accordance with the accompanying drawings.

An embodiment of an ejection apparatus or inhaler of the present invention will be described. The embodiment is constructed in hand-held form that can be carried with a user. The apparatus includes a memory unit for storing information about an individual user, such as data of user's case record and data of user's prescription, and information descriptive of relationships between liquid medicament cartridge tanks and liquid ejecting cartridges. Further, the apparatus is capable of ejecting a fixed amount of medicament as a plurality of liquid droplets with highly uniform particle size, and makes it allowable for the user to inhale the liquid droplets. For these purposes, the ejection cartridge includes an ejecting head for ejecting liquid droplets by means of thermal energy or piezoelectric energy.

Further, a mouthpiece, a liquid medicament cartridge tank, and a medicament ejection cartridge can be detachably loaded in a body part, or loading portion, of the ejection apparatus, so that the user can efficiently and sanitarily inhale the liquid medicament according to information of the prescription. The mouthpiece has an inhalation port through which the user inhales the medicament. The cartridge tank contains the liquid medicament. Data of the kind of medicament is attached to a distinguishing portion of the cartridge tank. Other information, such as manufacture number, use expiry period, and concentration of the liquid, may also be attached. Further, in addition to, or in place of information of the cartridge tank itself, information of an ejection cartridge to be interconnected with the cartridge tank can be attached to the distinguishing portion of the cartridge tank.

Also to a distinguishing portion of the ejection cartridge, data of the diameter of a nozzle of its ejecting head is attached. Likewise, other information, such as the number of nozzles, maybe attached. Furthermore, in addition to, or in place of information of the ejection cartridge itself, information of a liquid medicament cartridge tank to be interconnected with the ejection cartridge can be attached to the distinguishing portion of the ejection cartridge. Information to be attached varies depending on judging manner and judging matter of a later-described judging unit for identifying an ejection cartridge and/or a cartridge tank, or judging if the combination of an ejection cartridge and a cartridge tank is correct or wrong. Accordingly, information to be attached can be determined according to necessity or requirements.

As mentioned above, the ejection apparatus further includes an information reading unit or reader, and the judging unit for judging if the combination of the ejection cartridge and the cartridge tank is appropriate or inappropriate, or if each of the ejection cartridge and the cartridge tank loaded in their loading portions of the apparatus are correct or incorrect. When the judging unit judges everything is appropriate, the cartridge tank is moved toward the ejection cartridge. Thus, medicament contained in the tank by an elastic thin film bag surrounding the surface of the tank is fluidly interconnected with an ejecting head or ejecting portion of the ejection cartridge. Thus, it becomes possible to eject the liquid medicament supplied from the cartridge tank as droplets through the ejecting head. It may also be allowable to interconnect the cartridge tank and the ejection cartridge prior to their loading into the body part of the apparatus, and then load the connected unit in the apparatus. In this case, the connected combination is judged to be correct or incorrect.

Examples of judging manners by the judging unit can be various, as described in the following. In the case where an appropriate combination of a certain liquid medicament cartridge tank and a certain ejection cartridge is determined, and judgment of the combination can be performed based on data attached on the cartridge tank and data attached on the ejection cartridge, the judgment can be executed without reference to information stored in the memory unit. This judging manner is limited to a case where only the combination needs to be confirmed. In contrast thereto, in the case where each of the cartridge tank and the ejection cartridge needs to be confirmed if it is designated by data stored in the memory unit, or not, data read from the distinguishing portion of each of the cartridge tank and the ejection cartridge is compared with information stored in the memory unit.

The ejection apparatus can further include an ejection permitting unit for automatically permitting the ejecting head of the ejection cartridge to be operable only when the judging unit confirms that an appropriate cartridge tank and an appropriate ejection cartridge are loaded on their respective loading portions, or that an appropriate combination of the liquid cartridge tank and the ejection cartridge is loaded.

In the embodiment of the ejection apparatus, the cartridge tank and the ejection cartridge are separately prepared, and an ID (identification) code is attached to each of them. According to such an embodiment, erroneous use can be prevented by the structure of the ejection apparatus, and annoying or troublesome management by the user can be eliminated or reduced. Thus, the combination of a cartridge tank and an ejection cartridge can be appropriately managed readily by the user.

More specific embodiments will hereinafter be described with reference to the drawings.

A first specific embodiment of the present invention will be described referring to FIGS. 1 to 4. As illustrated in FIG. 1, a body case 1, a front cover 2, and an access cover 3 constitute the outside housing of an ejection apparatus or inhaler of this embodiment. The access cover 3 can be opened when a lock is released by a locking lever 5. Upon such release, a mouthpiece 4, a liquid medicament cartridge tank 6 (see FIG. 2), and a medicament ejection cartridge 7 (see FIG. 2) can be detachably installed in respective loading portions of a body part of the ejection apparatus. The mouthpiece 4 forms a flow passage through which a user inhales liquid medicament droplets with air.

Figure 2:
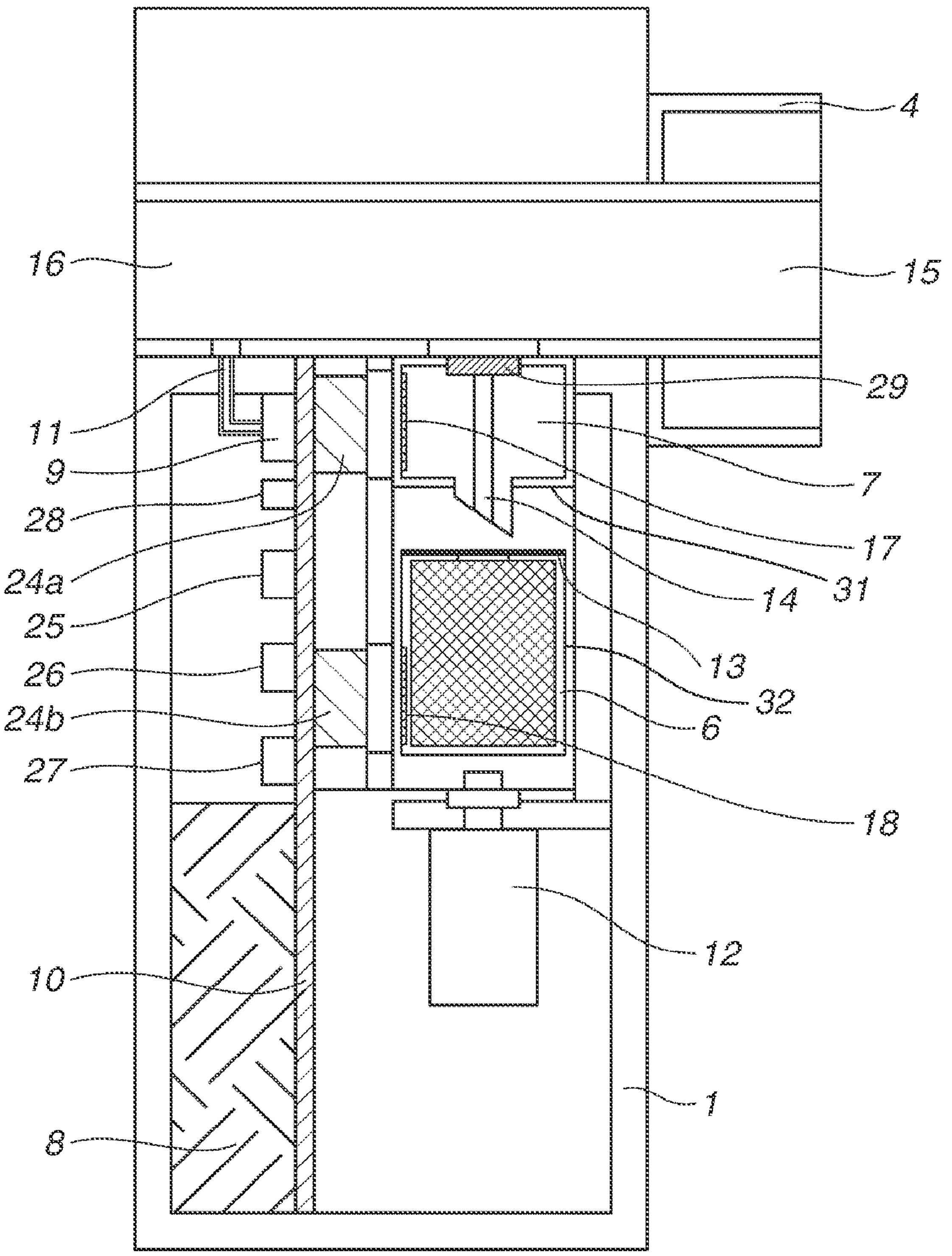
FIG. 2 is a cross-sectional view illustrating a condition of a first embodiment, in which a cartridge tank and a liquid ejection cartridge are not yet interconnected therewith, i.e., a condition prior to interconnection therebetween.

FIG. 2 shows a condition in which the access cover 3 is opened, and the mouthpiece 4, the cartridge tank 6, and the ejection cartridge 7 having an ejecting portion 29 are loaded. The inhaler includes a battery 8 for making it allowable for the user to carry and use the inhaler at any desired location. A negative pressure sensor 9 serving as an inhalation detector is disposed on a control substrate 10 that includes a CPU 25 for controlling a later-described operation of the inhaler. A pressure detecting port 11 of the sensor 9 is fluidly connected with the flow passage of the mouthpiece 4. The negative pressure sensor 9 detects inhalation by the user so that the ejection cartridge 7 can effectively eject droplets of liquid medicament responsive to the inhalation. The flow passage of the mouthpiece 4 extends from an air inlet port 16 to an inhalation port 15 for inhalation by the user.

The ejection cartridge 7 includes a memory 17 for storing, for example, information of the configuration of an ejecting head of the ejection cartridge 7, including the diameter of its nozzle, or its distinguishing or discriminating code. The memory 17 is preferably RFID, IC memory, or the like. Namely, it preferably allows the ejection cartridge 7 to be compact, i.e., does not greatly influence the size of the ejection cartridge 7. In another embodiment, a bar-code may be printed on the ejection cartridge 7. As such, the information can be read electromagnetically or optically, according to the above embodiments.

The cartridge tank 6 also includes a memory 18 attached on its side. The memory 18 is a storage medium for recording distinguishing data, such as RFID, IC memory, and bar-code. The memory 18 stores data, including for example the kind of medicament, so that medicament contained in the cartridge tank 6 can be distinguished or identified. To achieve its purpose, the storage medium for recording the distinguishing data can, for example, be capable of transmitting and receiving data in a non-contact manner, or can have electrical contacts, such as a contact-type IC card and a mechanical switch.

Readers 24*a* and 24*b* are disposed on the control substrate 10, corresponding to the memories 17 and 18 in which the distinguishing data is recorded. The readers 24*a* and 24*b* are arranged in such locations that correspond to positions of storage media of the loaded ejection cartridge 7 and cartridge tank 6, respectively. Thus, the readers 24*a* and 24*b* can read the data recorded in the memories 17 and 18, respectively. In this embodiment, a judging unit 26 disposed on the control substrate 10 compares the read distinguishing data with prescription data stored in a memory unit 27 in the body part of the inhaler.

When the judging unit 26 judges that the distinguishing data coincides with the prescription data, and each of the ejection cartridge 7 and the cartridge tank 9 is appropriate, a motor 12 for moving the tank is driven to move the cartridge tank 6 toward the ejection cartridge 7. The cartridge tank 6 has an elastic tank film 13 for preventing the outflow of liquid medicament. Accordingly, as the cartridge tank 6 moves toward the ejection cartridge 7, the tank film 13 is broken and penetrated by a liquid injection tube 14 of the ejection cartridge 7 with a sharpened tip end. The cartridge tank 6 is thus fluidly interconnected with the ejection cartridge 7.

Figure 3:
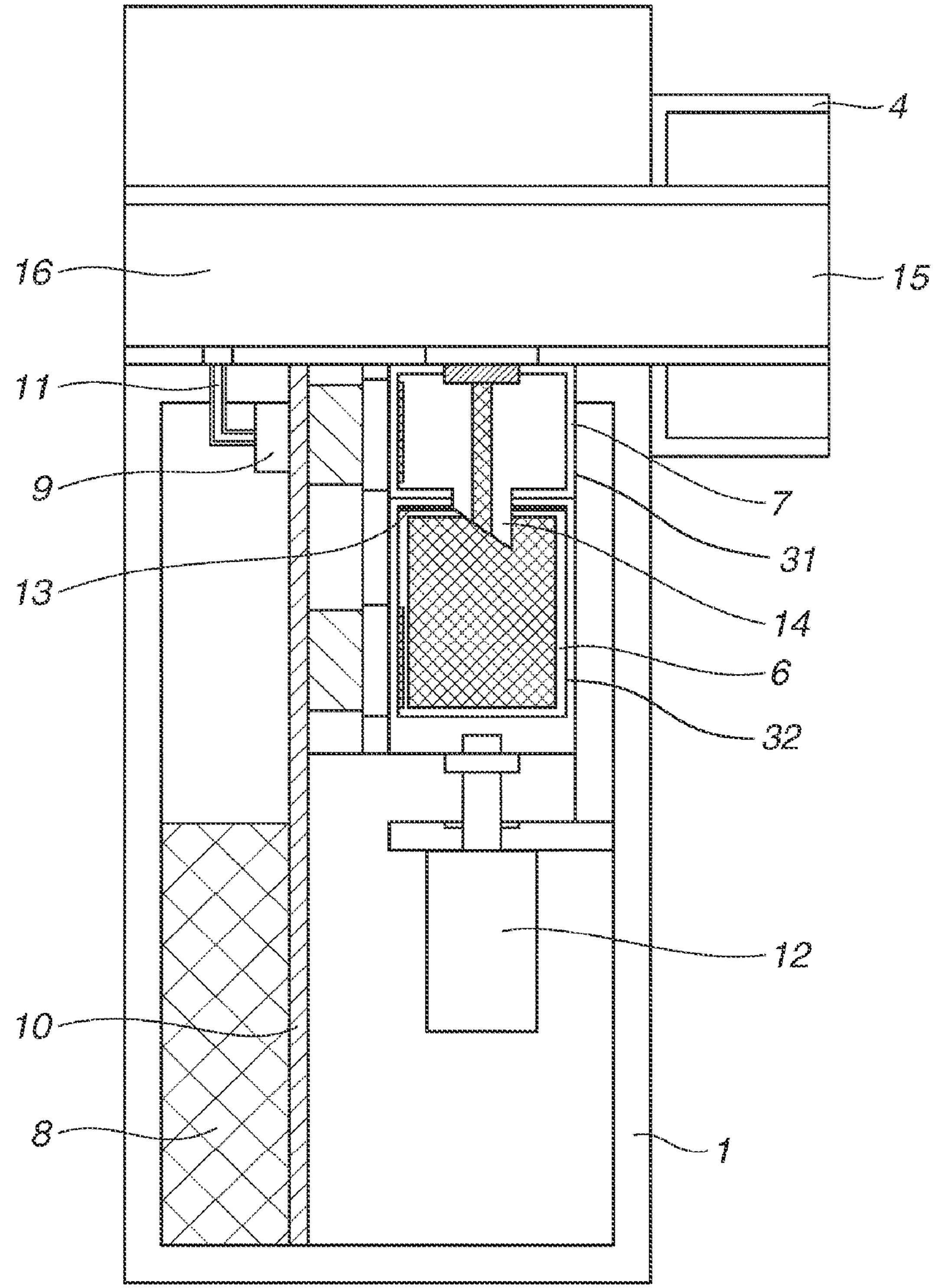
FIG. 3 is a cross-sectional view illustrating a condition of the first embodiment, in which inhalation is not yet executed by a user, i.e., a condition prior to inhalation by a user.

FIG. 3 illustrates a condition in which the cartridge tank 6 is fluidly interconnected with the ejection cartridge 7. The apparatus thus comes into a stand-by state during which the user is expected to start inhalation, and the apparatus generates a signal of sound, vibration, light or the like for informing the user of completion of inhalation preparation. In another embodiment, the apparatus may have a display portion of a liquid crystal device (LCD) or the like, and indicate "READY" or the like on the display portion.

Upon confirmation of the signal of completion of preparation, the user starts inhalation via the inhalation port 15 of the mouthpiece 4. Air is accordingly caused to flow in through the air inlet port 16. The negative pressure sensor 9 then detects a change in negative pressure occurring in the flow passage of the mouthpiece 4, through the pressure detection port 11. Upon detection of a predetermined negative pressure, the sensor 9 causes the ejection cartridge 7 to start ejection of medicament. Minute droplets of ejected medicament are, for example, droplets with diameters from three (3) microns to five (5) microns. Since specific gravity of the liquid is close to that of water, the droplet is very light and has little force of inertia. Hence, those droplets can easily ride the inhaled air flow, and reach user's lungs when their diameters are about 3 microns. When ejection of the medicament in the amount recorded in the prescription is completed, the apparatus awaits completion of inhalation of the medicament in the user's body, and generates a completion signal of inhalation to finish the user's inhalation. Upon completion of inhalation, the tank moving motor 12 is reversely rotated to separate the cartridge tank 6 from the ejection cartridge 7. The apparatus thus comes back into a condition in which both the cartridge tank 6 and the ejection cartridge 7 are removable from their respective loading portions 32 and 31.

Figure 4:
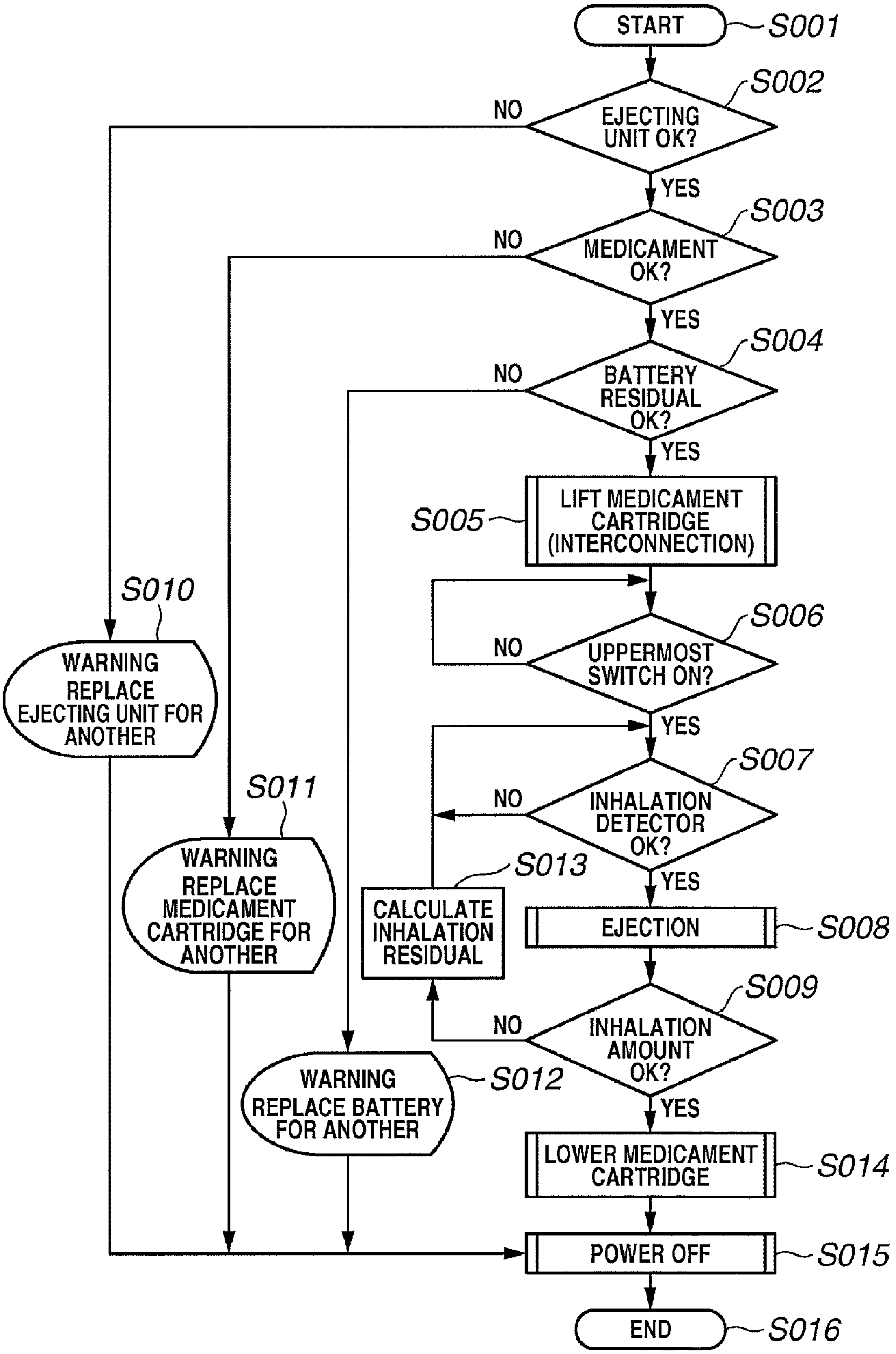
FIG. 4 is a flowchart showing an exemplified operation of the first embodiment.

FIG. 4 shows a flowchart of an exemplified operation of the first embodiment. Initially, when the user pushes a power switch, or takes some appropriate motion, the ejection apparatus comes into a use starting condition (step S001). After the use start, the apparatus checks the distinguishing code of the ejection cartridge 7, which is information stored in the memory 17, and includes data of the diameter of its head or ejecting unit (step S002). Unless the distinguishing code is coincident with data of the head diameter in the prescription data stored in the memory unit 27 in the body part of the ejection apparatus, the apparatus generates a warning for requiring replacement of the ejection cartridge 7 or the ejecting unit, and the operation is ended (step S010).

When data of the ejection cartridge 7 is found to be coincident with data of the head diameter in the prescription data, the apparatus then checks the distinguishing code of the cartridge tank 6, which is information stored in the memory 18, and includes data of medicament (step S003). Unless medicament data of the distinguishing code is coincident with data of medicament in the prescription data stored in the memory unit 27 in the body part of the ejection apparatus, the apparatus generates a warning for requiring replacement of the cartridge tank 7 or medicament cartridge, and the operation is ended (step S011). Here, it is allowable to repeat plural routines for executing the check, instead of ending the operation instantly as described above.

Here, an ejection permitting unit 28 (shown in FIG. 2) can be arranged, which automatically permits the operation of the ejection cartridge 7 only when data is coincident regarding both the ejection cartridge 7 and the cartridge tank 6. The ejection permitting unit 28 can be a means for permitting output of a head driving signal only when data is coincident regarding both the ejection cartridge 7 and the cartridge tank 6. Such means can be provided on the control substrate 10 including the CPU 25. In another embodiment, it is also allowable to adopt a structure in which when the data is coincident as above, the apparatus prompts the user to turn on an operation switch, for example.

By executing these steps, it is possible to confirm if the loaded medicament ejection cartridge and medicament cartridge container are appropriate, or not, and if their combination is appropriate, or not.

Then, the apparatus checks power remaining or residual of the battery 8 (step S004). When it is judged that the power residual of the battery 8 is no longer enough to carry out the medicament ejection, the apparatus executes a display of requiring replacement of the battery 8 (step S012).

When the residual power of the battery 8 is sufficient, the apparatus starts to drive the motor 12 for moving the cartridge tank 6 so that the cartridge tank 6 is lifted up to a position where the tank 6 is fluidly interconnected with the ejection cartridge 7 (step S005) An uppermost switch (not shown) for detecting an end position corresponding to the stop position of the motor 12 is disposed so that the cartridge tank 6 can be stopped at an appropriate location (step S006). Thus, medicament is supplied from the cartridge tank 6 to the ejection cartridge 7.

The apparatus thus takes a stand-by condition in which inhalation by the user is expected (step S007). Upon detection of inhalation by the user, medicament ejection from the ejection cartridge 7 is started (step S008). Here, the apparatus may execute a display for informing the user of the medicament ejection. Then, the negative pressure sensor 9 checks if an appropriate amount of inhalation is carried out, or not (step S009). When the amount of inhalation is less than necessary, or inhalation time is shorter than necessary, the apparatus calculates a shortage or inhalation residual (step S013), and returns to the stand-by condition in which inhalation is expected (step S007).

Upon completion of a predetermined ejection, the cartridge tank 6 is lowered, and separated from the ejection cartridge 7 (step S014). The cartridge tank 6 is thus moved to a position where it can be unloaded. Here, power supply from the electric power source is automatically turned off (steps S015/S016). However, prior to the turn-off, it is allowable to execute the check of battery residual as in the step S004, or record the inhalation process in memory unit 27 of the body part of the inhaler.

In ejection apparatuses such as the above-described embodiment, the following technical advantages can be achieved. The individual user can carry out self-administration of medicament without any pain and paying special attention to the medicament, and management and use manner of the ejecting head. The above-described ejection apparatus can thus make it possible that users, even increasing elderly people, readily and accurately perform appropriate inhalation.

In order for users to choose a correct combination of the ejection cartridge and the cartridge tank, the ejection cartridge and the cartridge tank can be assembled into a single integral unit. However, such a construction suffers the following disadvantage in a case of insulin or the like where the medicament needs to be dosed to a patient, such as a diabetic, at every meal, for example. In the case of insulin or the like, the user usually goes out every morning carrying a medicament ejection apparatus to which a liquid medicament cartridge tank containing one day's portion of medicament is installed, and the user loads or replaces only a medicament ejection cartridge at the time of inhalation. The reason therefor is that the ejection cartridge is required to be disposed of every time after used, similar to the using manner of a needle of a syringe, while the medicament is used several times. This is because there is a possibility that medicament containing protein changes in quality or coagulates when exposed to air. Accordingly, when the ejection cartridge and the cartridge tank are assembled into an integral kit, the entire kit must be disposed of every time after used. Such disadvantage can be eliminated by the above embodiment.

Further, in the above embodiment, even when inhalation of plural medicaments is executed at the time of inhalation, the ejection apparatus can be repeatedly used plural times after exchange of only the cartridge tank with another, since the ejection cartridge can be used without being exchanged. Furthermore, when the same medicament is applied to different parts of a body of the user, it is possible to achieve efficient dosing of the medicament to different parts by exchanging only the ejection cartridge. Thus, also in those cases, the possibility of erroneous inhalation due to inappropriate loading of the ejection cartridge and the cartridge container can be eliminated. It is hence possible to provide an inhaler which is noticeably convenient in use, and users can use without any anxiety.

A second embodiment of an ejection apparatus will be described with reference to FIGS. 5 to 8. In the first embodiment, the liquid medicament cartridge tank 6 and the medicament ejection cartridge 7 have distinguishing information for comparison with information in the memory unit 27 in the body part of the ejection apparatus, respectively. In contrast, in the second embodiment, distinguishing data is attached only to one of the cartridge tank 6 and the ejection cartridge 7, and this information is compared with information stored in the memory unit 27. Confirmation of appropriateness of the other, or combination is indirectly carried out by a later-described coupling means.

Figure 5:
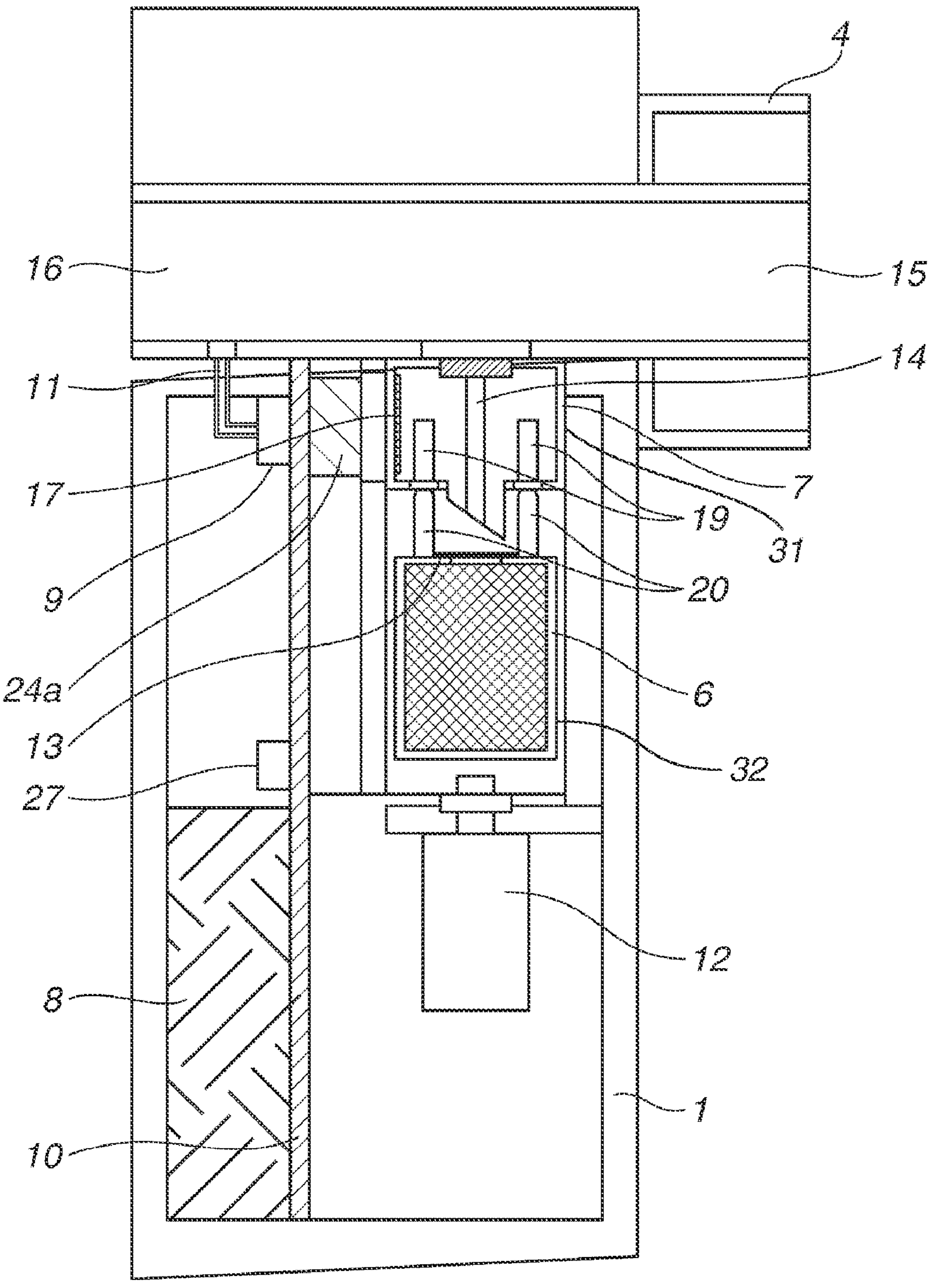
FIG. 5 is a cross-sectional view illustrating a condition of a second embodiment, in which a cartridge tank and a liquid ejecting cartridge are not yet interconnected therewith, i.e., a condition prior to interconnection therebetween.

FIG. 5 illustrates a structure in which only the ejection cartridge 7 is equipped with a storage medium 17 for recording distinguishing information, and confirmation of appropriateness of the cartridge tank 6 is indirectly carried out by the shape of its coupling means corresponding to the coupling means of the ejection cartridge 7. Here, a recess portion 19 is formed in the ejection cartridge 7, and a protruding portion 20 corresponding to the recess portion 19 is formed in the cartridge tank 6.

An exemplified operation of the structure illustrated in FIG. 5 is executed in the following manner. After the mouthpiece 4, the cartridge tank 6, and the ejection cartridge 7 are loaded in their respective loading portions 32 and 31, the reader 24*a* reads data in the storage medium 17 of the ejection cartridge 7. Then, comparison of data is performed as described in the first embodiment. When the comparison result is OK, the tank driving motor 12 is driven to fluidly connect the cartridge tank 6 with the ejection cartridge 7. Here, unless the shape of the coupling means of the cartridge tank 6 corresponds to that of the ejection cartridge 7, the cartridge tank 6 cannot be moved to a location where it is interconnected with the ejection cartridge 7, because of inappropriate combination of the coupling means. The ejection cartridge 7 is therefore unable to eject the liquid medicament.

In the above structure, it is preferable to dispose a switch (not shown) at a motion completion location of the cartridge tank 6, where the ejection cartridge 7 is positioned, and take a signal for indicating appropriateness of the combination of the coupling means of the cartridge tank 6 and the ejection cartridge 7. Unless the motion completion switch turns on in a predetermined period, the apparatus judges that the combination is inappropriate, and does not permit ejection of the liquid medicament.

Figure 6:
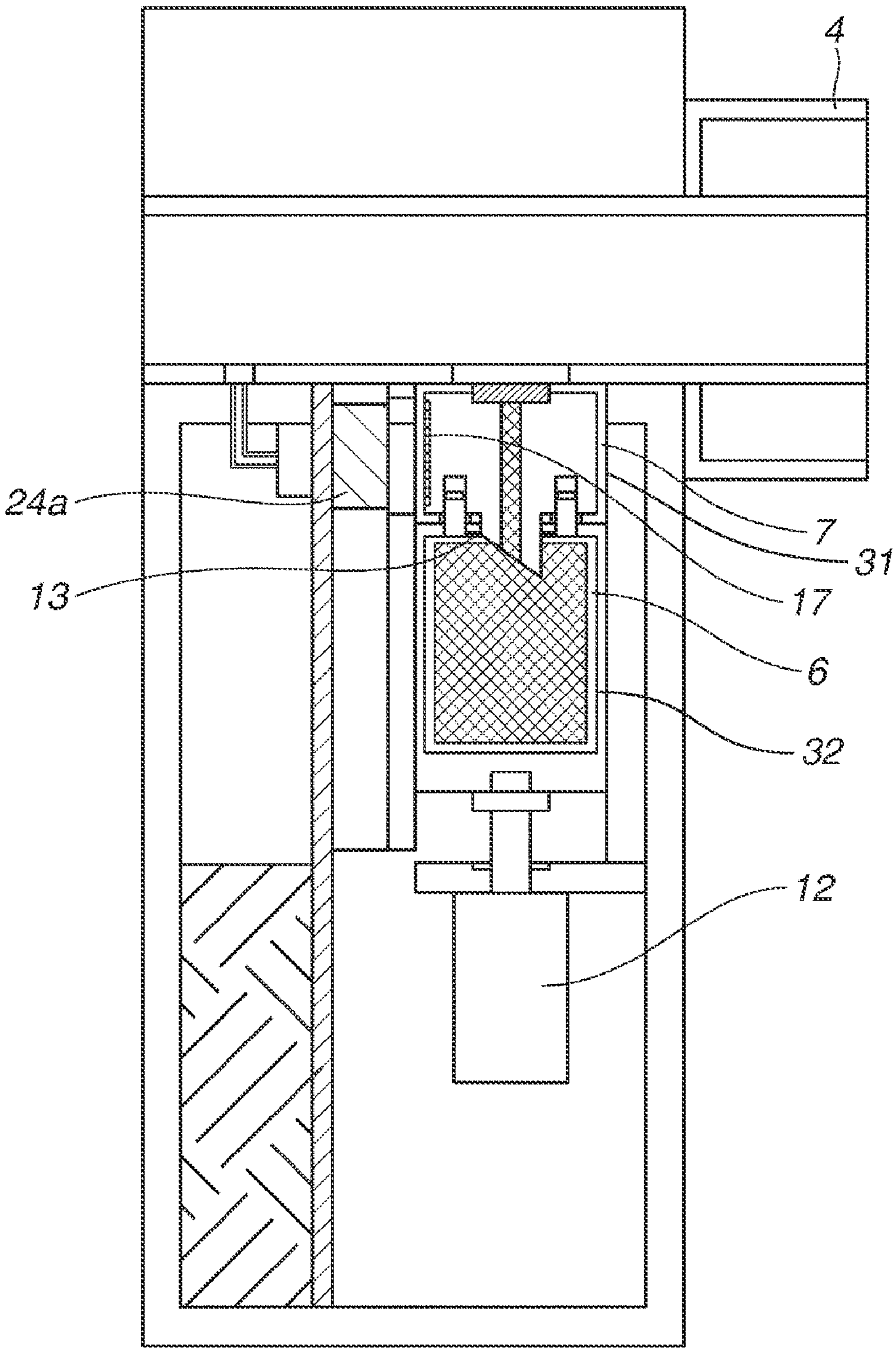
FIG. 6 is a cross-sectional view illustrating a condition of the second embodiment, in which inhalation is not yet executed by a user, i.e., a condition prior to inhalation by a user.

When the coupling means of the cartridge tank 6 and the ejection cartridge 7 correspond to each other as illustrated in FIG. 6, the cartridge tank 6 and the ejection cartridge 7 are fluidly interconnected, and a stand-by condition for prompting inhalation is established.

Figure 7:
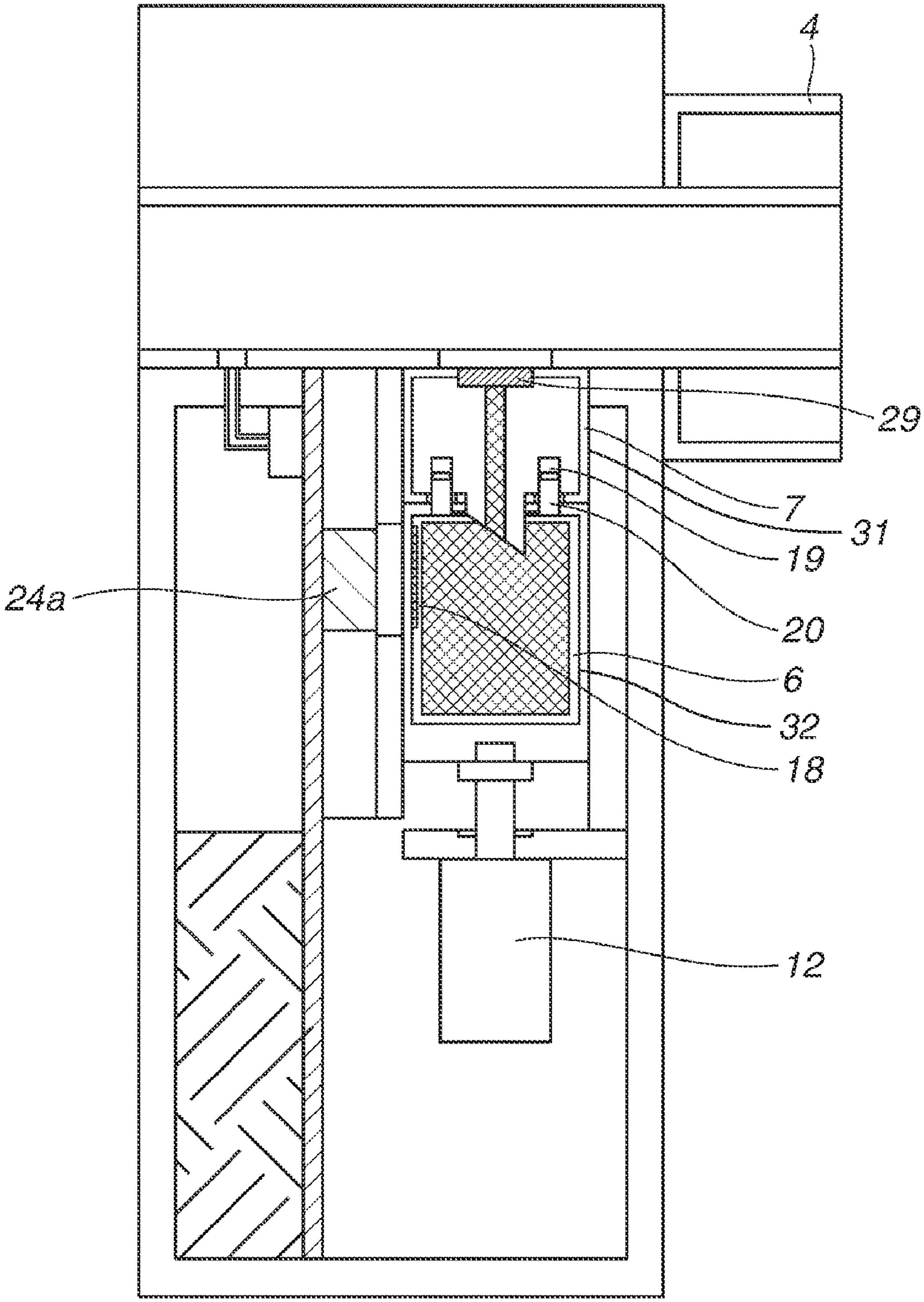
FIG. 7 is a cross-sectional view illustrating the second embodiment using a cartridge tank with a distinguishing or discriminating code.

FIG. 7 illustrates a structure in which only the cartridge tank 6 is equipped with a storage medium 18 for recording distinguishing information. Also in this structure, appropriateness of the combination of the cartridge tank 6 and the ejection cartridge 7 is judged by shapes of the recess and protruding portions 19 and 20 of the coupling means. When the shapes of the recess and protruding portions 19 and 20 correspond to each other, the cartridge tank 6 is moved to the motion completion location by the motor 12. The data in the storage medium 18 of the cartridge tank 6 is then read by the reader 24*b*, and the comparison of data is performed as described in the first embodiment. Depending on the comparison result, the apparatus decides if ejection from the ejection cartridge 7 should be executed, or not. Also in this structure, like the structure of FIGS. 5 and 6, it is possible to read the data in the storage medium 18 of the cartridge tank 6 in its loading position, and compare the data as described in the first embodiment.

Figure 8:
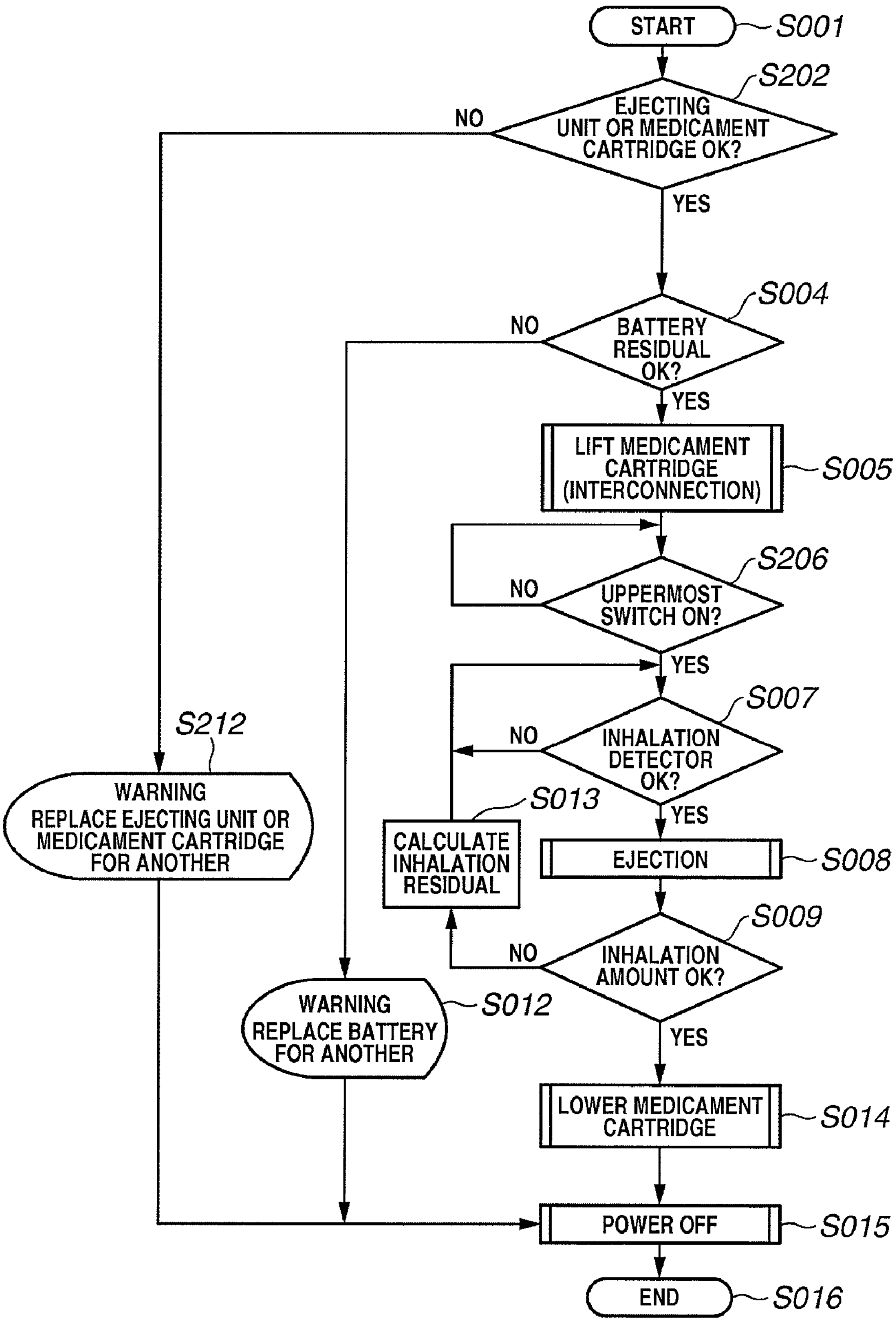
FIG. 8 is a flowchart showing an exemplified operation of the second embodiment.

FIG. 8 shows a flowchart of an exemplified operation of the second embodiment. This operation differs from that of the first embodiment in a reading step S202 of reading the distinguishing code (information stored in the memory) of the cartridge tank 6 or the ejection cartridge 7. Other operations of the second embodiment are the same as those of the first embodiment. In the flowchart of the operation of the second embodiment, however, it is allowable to generate a warning when the uppermost end switch cannot be turned on in the step (S206) and to add a step of requiring replacement of the cartridge tank 6 or the ejection cartridge 7 whose distinguishing code is not judged (step S212).

In the above structure, the recess and protruding portions 19 and 20 are used as the coupling means; however, configurations of the coupling means are not limited thereto. For example, the following structure can be used. In this structure, both the cartridge tank 6 and the ejection cartridge 7 are equipped with magnets, and when the combination of the cartridge tank 6 and the ejection cartridge 7 is appropriate, corresponding magnets on the cartridge tank 6 and the ejection cartridge 7 are brought into coupled contact by attracting force to achieve completion of connection therebetween.

In the above description, the cartridge tank 6 and the ejection cartridge 7 are installed to the body part of the inhaler in a separate manner. It is, however, possible to adopt a loading manner in which coupling between the cartridge tank 6 and the ejection cartridge 7 is tried prior to their loading to the body part, and an appropriately-coupled kit is then loaded in the body part of the inhaler. In this case, the cartridge tank 6 is not moved after loading (accordingly, the motor 12 can be omitted), and the distinguishing data attached to one of the cartridge tank 6 and the ejection cartridge 7 is judged. In this case, the flowchart of an operation is shown in FIG. 8, with the exception that the steps S005, S206 and S014 are omitted.

By executing the steps described above, it is possible to judge if the loaded medicament ejection cartridge and liquid medicament cartridge container are appropriate, or not, and if their combination is appropriate, or not.

Figure 9:
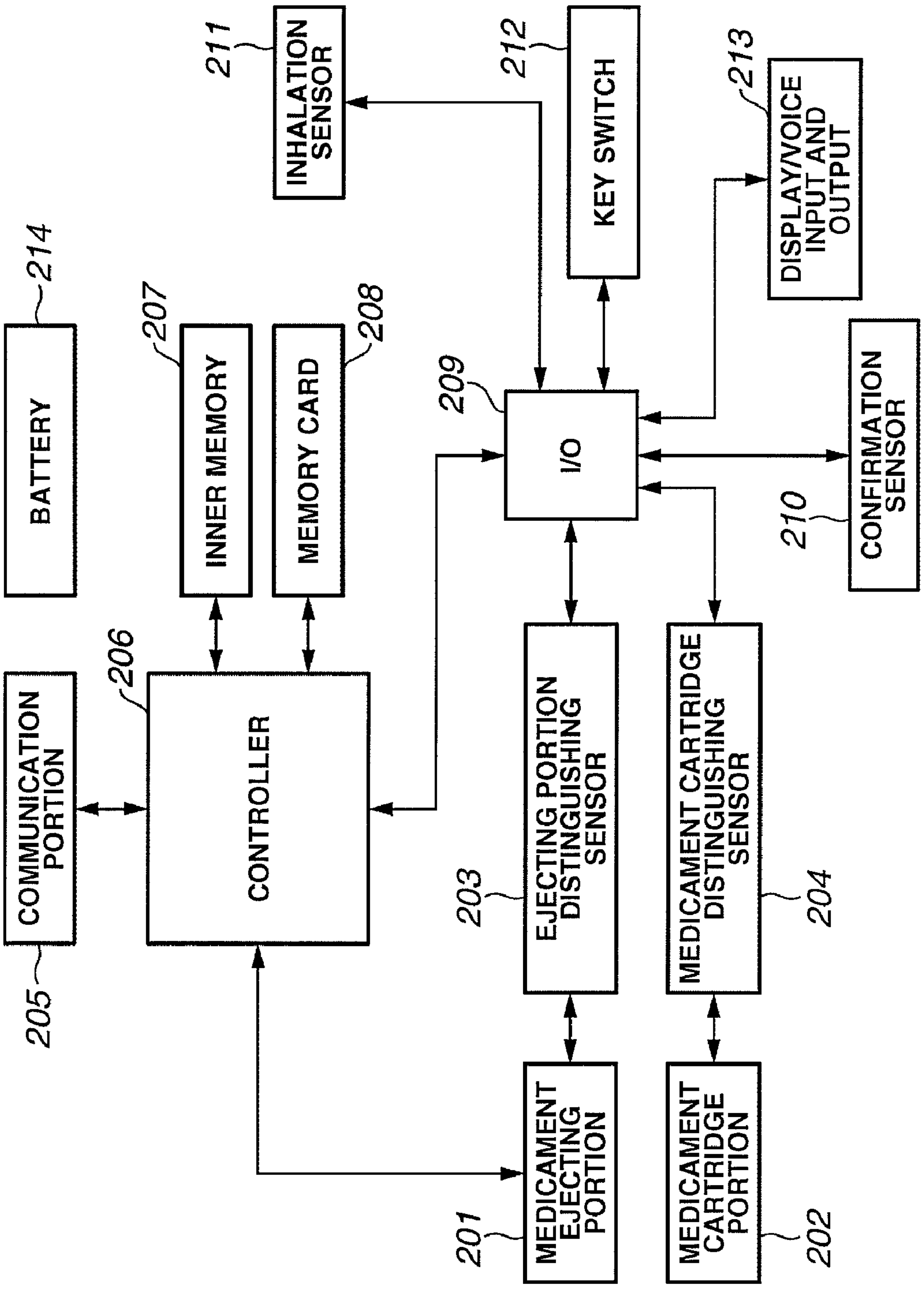
FIG. 9 is a block diagram illustrating a third embodiment.

A third embodiment will be described with reference to FIGS. 9 to 11. FIG. 9 shows the structure of a body part of an inhaler of this embodiment. The body part includes a controller 206 containing a CPU for controlling the entire apparatus, a communication portion 205 for executing wireless communications, an internal storage memory 207, or inner memory, for storing control processes and various data, and a detachable memory card 208 for storing information regarding an individual user. It further includes an I/O interface 209, a key switch 212, including a ten-key switch or the like, an input/output portion 213 using display and sound or voice (a display/voice input and output), such as LC (liquid crystal) display, microphone, speaker or the like, and a confirmation sensor 210 for recognizing or confirming a living body. Furthermore, there are also arranged in the body part of the apparatus an ejector distinguishing sensor 203 for distinguishing information of a medicament ejection cartridge, a container distinguishing sensor 204 for distinguishing information of the kind of medicament or the like, an inhalation sensor 211 for detecting inhalation by the user, and a rechargeable battery 214 serving as an electric power source. A liquid medicament cartridge tank or portion 202 for containing liquid medicament, and a medicament ejection cartridge or portion 201 for ejecting droplets of medicament supplied from the cartridge tank 202 are detachably loadable in respective loading portions of the body part of the apparatus.

The ejection cartridge 201 has distinguishing information of the diameter of a nozzle of the ejecting head, and the cartridge tank 202 has information of the kind of medicament. The communication portion 205 is so constructed that wireless communications according to an appropriate communication method, and wireless data communications with an external database can be executed by the ten-key in the key switch 212, and the input/output portion 213. A method of the wireless communications can be, for example, a method adopted in mobile communications (cellular phone, car phone, PHS (personal handyphone system), etc.), a method using satellite communications, a method using Bluetooth, or a Zig-bee method. The internal memory 207 can be a read-only medium, such as ROM, and is more preferably a rewritable flash memory or the like, which enables renewal or modification of a program via the communication portion 205. The memory card 205 is a storage medium, such as a semiconductor record medium, MO, CD-R, CD-RW, DVD, and FD, that is rewritable and detachably loadable. The I/O interface 209 is so constructed that an external input-output device, such as various kinds of measurement sensors and printers, can be selectively connected thereto according to the user's need to measure blood pressure, pulsation, blood sugar level, temperature, etc, or to print out measured data.

The recognition or confirmation sensor 210 executes a living-body recognition of the user by means of fingerprint, voiceprint, face, blood vessel pattern of iris retina, venous pattern, or the like so that only an individual registered in the inhaler can use the apparatus. The inhaler is so constructed that information, such as ID, code number, and password, needs to be input to operate the inhaler. The living-body recognition can also be employed in addition to the above input of information. According to such construction, the user's recognition is performed in a step S304 as illustrated in FIG. 11 showing a flowchart of inhalation operation of the third embodiment. Thus, a user or users permitted to use the inhaler is limited, and erroneous inhalation by others is accordingly prevented. The third embodiment differs from the first embodiment in steps S304, S317, S318, and S319. The third embodiment is the same as the first embodiment in other respects.

In the third embodiment, the above-described ejection permitting unit permits the ejecting head of the ejection cartridge to be operable only when data of living-body features of the user stored in the memory unit 27 is coincident with data from the recognition sensor 210.

Figure 10:
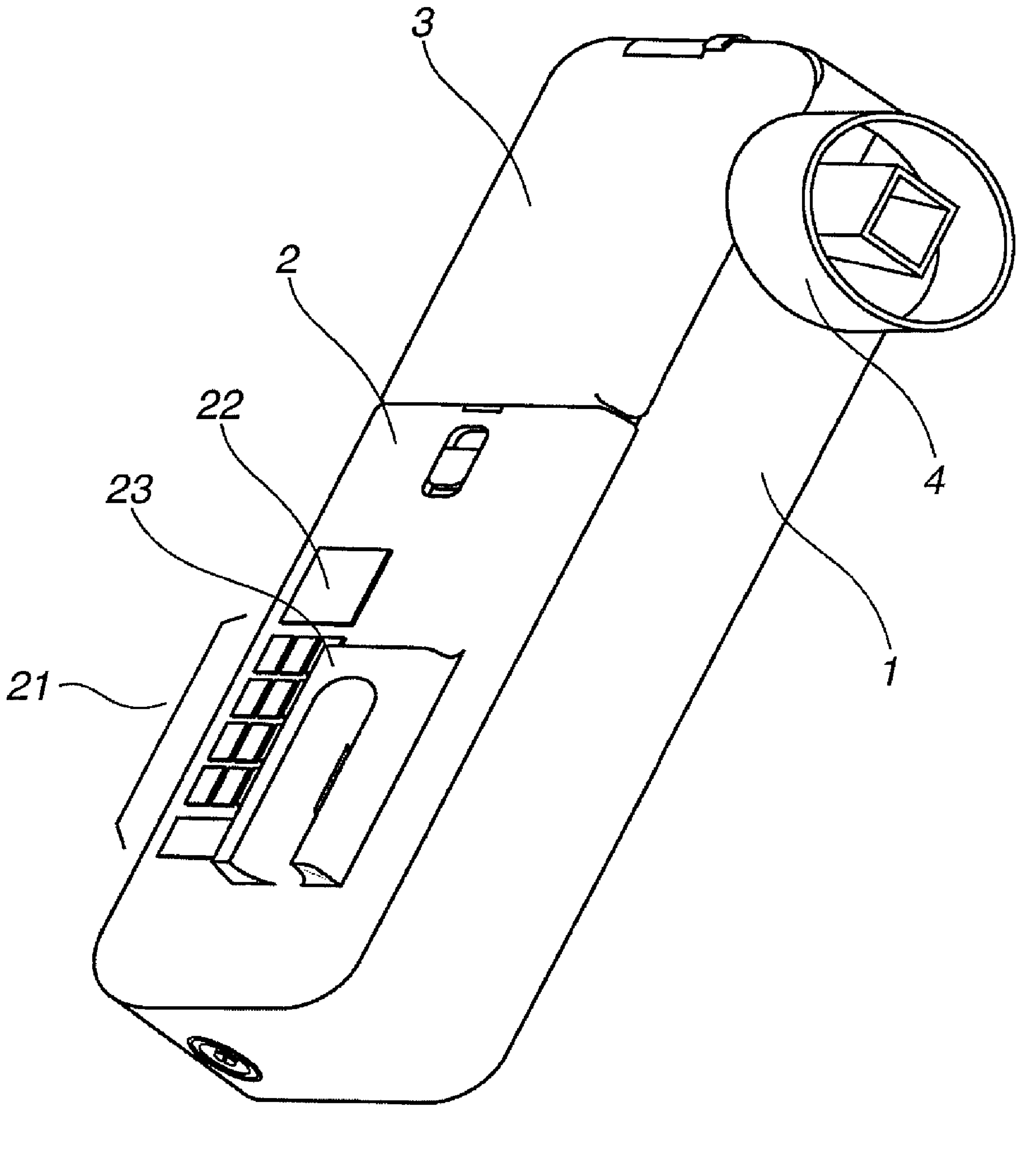
FIG. 10 is a perspective view schematically illustrating the outside appearance of the third embodiment.
Figure 11:
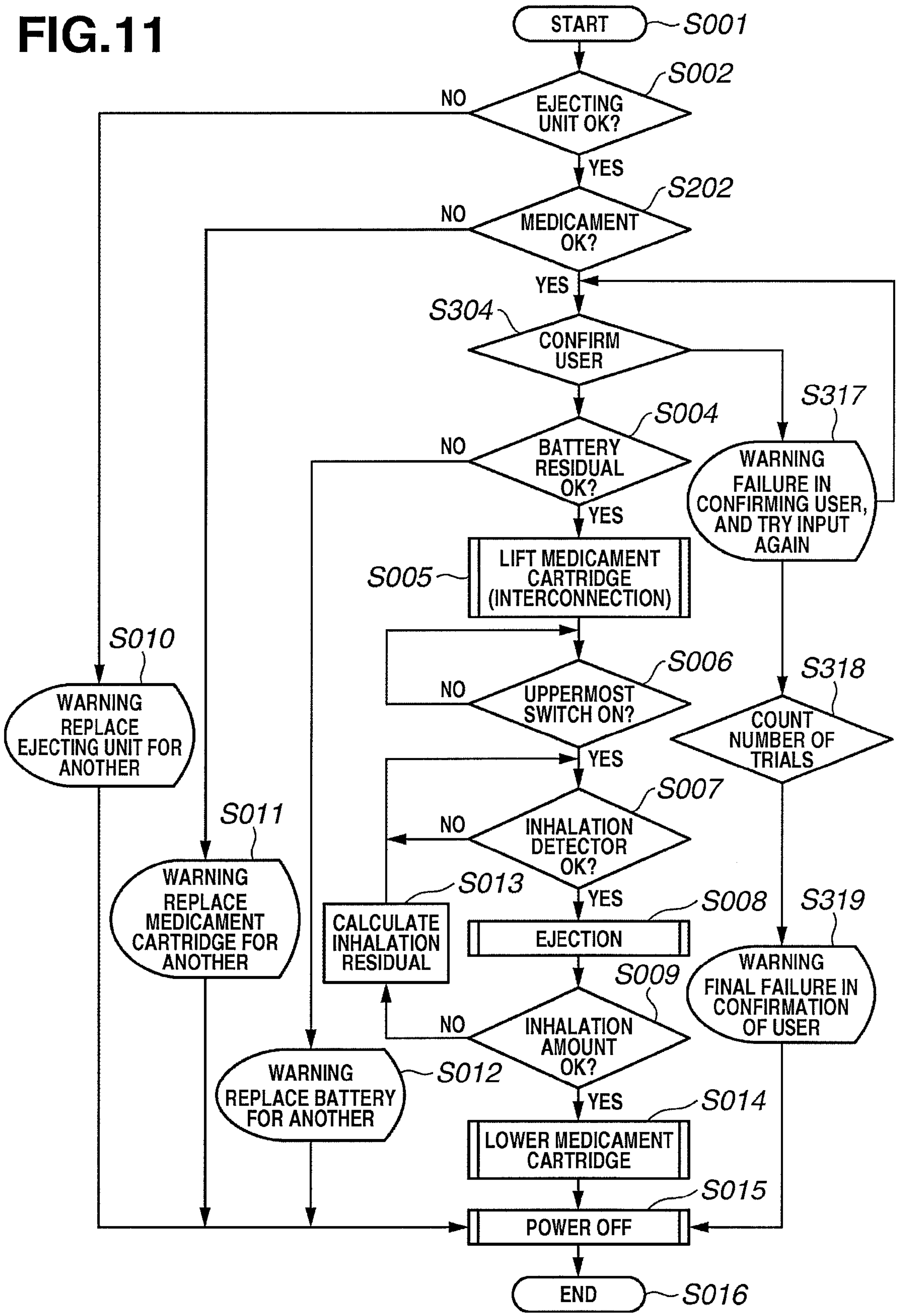
FIG. 11 is a flowchart showing an exemplified operation of the third embodiment.

As illustrated in FIG. 10, the inhaler of this embodiment can be equipped with a fingerprint recognition sensor 23 disposed on a front face of the apparatus as the living-body recognition sensor, a ten-key 21 usable to input ID, password, or code number into the apparatus, and an LC display unit 22 disposed as the display unit, for example.

Ejection apparatuses of the present invention can be typically employed as the above-discussed inhaler, but its application is not limited to inhalers. Ejection apparatuses of the present invention can also be used as apparatuses for simply ejecting liquid of medicament or the like for purposes of eyewash, etc. Further, liquid to be ejected is typically liquid medicament, but the liquid may be liquid of personal taste, liquid of flavor, etc. The present invention can be widely applied to such ejecting apparatuses as require appropriate combinations of liquid cartridge containers and ejection cartridges.

Except as otherwise disclosed herein, the various components shown in outline or in block form in the figures are individually well-known and their internal construction and operation are not critical either to the making or using of the present invention or to a description of the preferred mode of the invention.

The present invention is not limited to the above embodiments, and various changes and modifications can be made within the spirit and scope of the present invention. Therefore, to apprise the public of the scope of the present invention, the following claims are made.

This application claims priority from Japanese Patent Application No. 2005-290603, filed Oct. 4, 2005, the contents of which are hereby incorporated by reference.

What is claimed is:

1. An ejection apparatus for ejecting droplets of liquid comprising:

a loading portion constructed to detachably load therein a liquid cartridge container for containing a liquid, and a liquid ejection cartridge having ejecting nozzles for ejecting the liquid;

at least one reader constructed to read information, including first information attached to the liquid cartridge container and second information attached to the liquid ejection cartridge; and a judging unit constructed to judge, based on the information read by the at least one reader, at least one of (i) whether the liquid cartridge container is a predetermined liquid cartridge container and the liquid ejection cartridge is a predetermined liquid ejection cartridge, and (ii) whether a combination of the liquid cartridge container and the liquid ejection cartridge is a predetermined combination, wherein the first information attached to the liquid cartridge container includes information regarding a kind of the liquid contained in the liquid cartridge container or information regarding the liquid ejection cartridge which is suitable to be interconnected with the liquid cartridge container, and wherein the second information attached to the liquid ejection cartridge includes information regarding a diameter of the ejecting nozzles.

2. An ejection apparatus for ejecting droplets of liquid comprising:

a loading portion constructed to detachably load therein a liquid cartridge container for containing a liquid, and a liquid ejection cartridge having ejecting nozzles for ejecting the liquid, each of the liquid cartridge container and the liquid ejection cartridge having a coupler that allows interconnection between the liquid cartridge container and the liquid ejection cartridge only when a combination of the liquid cartridge container and the liquid ejection cartridge is a predetermined combination;

at least one reader constructed to read information attached to one of the liquid cartridge container and the liquid ejection cartridge which are interconnected with each other by the coupler; and a judging unit constructed to judge, based on the information read by the at least one reader, whether the liquid cartridge container is a predetermined liquid cartridge container and the liquid ejection cartridge is a predetermined liquid ejection cartridge, wherein the information attached to the liquid cartridge container includes information regarding a kind of the liquid contained in the liquid cartridge container or information regarding the liquid ejection cartridge which is suitable to be interconnected with the liquid cartridge container, and wherein the information attached to the liquid ejection cartridge includes information regarding a diameter of the ejecting nozzles.

3. An ejection apparatus according to claim 1, further comprising a memory unit, and wherein the judging unit judges based on a comparison between the information read by the at least one reader and information stored in the memory unit.

4. An ejection apparatus according to claim 2, further comprising a memory unit, and wherein the judging unit judges based on a comparison between the information read by the at least one reader and information stored in the memory unit.

5. An ejection apparatus according to claim 1, further comprising an ejection permitting unit constructed to permit the ejecting nozzles of the liquid ejection cartridge to be operable only when the judging unit confirms that the liquid cartridge container is the predetermined liquid cartridge container and the liquid ejection cartridge is the predetermined liquid ejection cartridge, or that the combination of the liquid cartridge container and the liquid ejection cartridge is the predetermined combination.

6. An ejection apparatus according to claim 2, further comprising an ejection permitting unit constructed to permit the ejecting nozzles of the liquid ejection cartridge to be operable only when the judging unit confirms that the liquid cartridge container is the predetermined liquid cartridge container and the liquid ejection cartridge is the predetermined liquid ejection cartridge.

7. An ejection apparatus according to claim 5, further comprising a recognition sensor constructed to perform a living-body recognition of a user, and wherein the ejection permitting unit permits the ejecting nozzles of the liquid ejection cartridge to be operable only when information of living-body features of the user stored in a memory unit is coincident with information from the recognition sensor.

8. An ejection apparatus according to claim 6, further comprising a recognition sensor constructed to perform a living-body recognition of a user, and wherein the ejection permitting unit permits the ejecting nozzles of the liquid ejection cartridge to be operable only when information of living-body features of the user stored in a memory unit is coincident with information from the recognition sensor.

9. An ejection apparatus according to claim 1, wherein the at least one reader reads information electromagnetically or optically.

10. A liquid ejection cartridge loadable on an ejection apparatus together with a liquid cartridge container containing a liquid, the liquid ejection cartridge comprising:

ejecting nozzles constructed to eject liquid; and a portion with information of at least one of the liquid ejection cartridge and the liquid cartridge container that is to be interconnected with the liquid ejection cartridge, wherein the information of the liquid ejection cartridge includes information regarding a diameter of the ejecting nozzles.

11. A liquid ejection cartridge according to claim 10, further comprising a coupler capable of being coupled only to a corresponding coupler of a liquid cartridge container that constitutes a predetermined combination with the liquid ejection cartridge.

12. An ejection apparatus according to claim 1, wherein the liquid ejection cartridge includes an ejecting head for ejecting liquid droplets by means of thermal energy or piezoelectric energy.

13. An ejection apparatus according to claim 2, wherein the liquid ejection cartridge includes an ejecting head for ejecting liquid droplets by means of thermal energy or piezoelectric energy.

* * * * *